(12) United States Patent
Fitzgerald

(10) Patent No.: US 7,402,796 B2
(45) Date of Patent: Jul. 22, 2008

(54) METHOD AND APPARATUS FOR MONITORING DEPOSITION OF SOLIDS IN PIPELINES USING A PLURALITY OF RADIATION SOURCES POINTING TO A UNIQUE DETECTOR

(75) Inventor: John Barry Fitzgerald, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 280 days.

(21) Appl. No.: 10/540,967

(22) PCT Filed: Dec. 18, 2003

(86) PCT No.: PCT/GB03/05545

§ 371 (c)(1),
(2), (4) Date: Oct. 20, 2005

(87) PCT Pub. No.: WO2004/059304

PCT Pub. Date: Jul. 15, 2004

(65) Prior Publication Data

US 2006/0131496 A1   Jun. 22, 2006

(30) Foreign Application Priority Data

Dec. 31, 2002 (GB) .................. 0230324.6

(51) Int. Cl.
*G01V 5/00* (2006.01)
(52) U.S. Cl. .................. 250/253; 250/373; 73/32 R
(58) Field of Classification Search ................ 250/253, 250/373; 73/32 R
See application file for complete search history.

(56) References Cited

U.S. PATENT DOCUMENTS

| 3,846,631 A | * | 11/1974 | Kehler ..................... 250/269.3 |
| 4,539,649 A | | 9/1985 | Michaelis et al. |
| 4,667,515 A | * | 5/1987 | Farren et al. .................. 73/601 |
| 4,885,759 A | | 12/1989 | Tomoda et al. |
| 5,166,964 A | * | 11/1992 | Hasegawa et al. ............. 378/89 |
| 5,479,020 A | | 12/1995 | Mohn |
| 6,097,786 A | | 8/2000 | Groves et al. |

FOREIGN PATENT DOCUMENTS

| EP | 0 316 048 A2 | 5/1989 |
| GB | 2 168 150 A | 6/1986 |
| GB | 2 200 206 A | 7/1988 |
| WO | 94/25859 A1 | 11/1994 |
| WO | 97/29356 A1 | 8/1997 |

* cited by examiner

*Primary Examiner*—Christine Sung
(74) *Attorney, Agent, or Firm*—Steven Gahlings, Esq.; James McAleenan, Esq.; Jody DeStefanis, Esq.

(57) ABSTRACT

The invention concerns a method of monitoring flow in a flow pipe. According to the invention, the method comprising the following steps: providing a flow pipeline having a unique photon detector at a first position on the periphery of said pipe, a first photon source at a second position on the periphery of of said pipe, said detector and first source defining a first chord across said pipe, and one or more additional photon sources at positions on the periphery of said pipe defining one or more additional chords across said pipe; determining the density across said first chord from the count rate detected from the first source by the detector; and determining the densities across said one or more additional chords from the count rate detected from the one or more additional sources by the detector in order to determine the deposition of solid in the pipe.

16 Claims, 3 Drawing Sheets

US 7,402,796 B2

METHOD AND APPARATUS FOR MONITORING DEPOSITION OF SOLIDS IN PIPELINES USING A PLURALITY OF RADIATION SOURCES POINTING TO A UNIQUE DETECTOR

FIELD OF INVENTION

The invention relates to flow assurance, and more specifically to methods and apparatus for monitoring solids and/or fluids in pipeline flows. This is particularly useful in the detection and/or prediction of deposition of solids in multiphase or mixed pipeline flows.

BACKGROUND OF INVENTION

The use of gamma-ray densitometers calibrated for use as hold-up meters, to measure flow and hold-up in pipelines is well known. Examples include Schlumberger™'s Vx technology and the FloWatcher™ Densitometer (FWD). Schlumberger's Vx technology uses low-energy gamma rays (PE) measurements. These measurements may encounter several difficulties in monitoring solids in mixed flow pipelines.

Low-energy gamma rays do not go through metallic walls of a sufficient thickness. Pipelines are generally made of steel. As a result, signal attenuation is very high leading for pipelines of typical diameters, which, in addition, contain a flow of high-density materials such as bitumen, water and particulates and a low gas fraction. This leads to a low count rate in the PE counting window.

Furthermore, bitumen contains significant quantities (typically 10-1,000 ppm) of elements such as vanadium ($Z=23$) and nickel ($Z=28$), which have an atomic number Z much higher than the atomic numbers found in hydrocarbon and water ($H=1$, $C=6$, $O=8$). Sulphur ($Z=16$) may also be present at percentage levels. The attenuation cross-section for low-energy photons is proportional to $Z^4$. Therefore, small quantities of bitumen with uncertain content can strongly affect the measured PE attenuation. This is similar to the problem encountered in some surface monitoring applications, where inorganic scale in the flow-meter pipe can give large errors in the measured fluid PE cross-section due to the presence of higher-Z elements such as barium, sulphur and calcium.

Bitumen is viscous and sticky and may also adhere to the low-attenuation transmission windows required for PE measurement through a pipeline. This introduces further errors and loss of flux for a dual-energy measurement. The degree of adhesion may depend on both the bitumen properties and the window material.

SUMMARY OF INVENTION

An object of the invention is to provide improved methods for the monitoring the flow and deposition of solids in pipeline flows.

Accordingly, an aspect of the invention provides a method of monitoring flow in a flow pipe, the method comprising: providing a flow pipe having
   a photon detector at a first point on the periphery of said pipe,
   a first photon source at a second position on the periphery of said pipe, said detector and first source defining a first chord across said pipe, and
   one or more additional photon sources at positions on the periphery of said pipe, said detector and one or more additional sources defining one or more additional chords across said pipe;
   determining the density across said first chord as a function of count rate detected from the first source by the detector; and
   determining the densities across said one or more additional chords as a function of count rate detected from the one or more additional sources by the detector.

An advantage of the method is that it allows the average phase fractions within the flow and the deposition of solid, such as sand, in the pipe to be determined.

Methods may also be used to provide a warning of potential deposition by measuring the tendency of solid in said pipeline to gravitate to a lower part of the flow.

In some embodiments, the first source is positioned diametrically opposite the detector. For example, the detector is positioned at the uppermost point on the periphery of the pipe and the first source is positioned at the lowermost point on the periphery of the pipe.

In some embodiments, the one or more additional sources may comprise one or more pairs of identical photon sources,
   each said pair of sources being positioned on the periphery of the pipe such that the chords across the pipe defined by each member of the pair with the detector are of equal length,
   average flow or hold-up being determined from the average value of the densities across said chords.

In other embodiments, the one or more additional sources may comprise at least one pair of non-identical sources positioned on the periphery of said pipe such that the chords across the pipe defined by each member of the pair with the detector are of equal length, the asymmetric deposition of solid in the pipe being determined from the relative density values determined across the chords defined by each member of the pair with the detector.

Another aspect of the invention provides an apparatus for monitoring solids in a mixed flow pipe comprising;
   a photon detector adapted for attachment at a first point on the periphery of said pipe;
   a first photon source adapted for attachment at a second point on the periphery of said pipe, said detector and first source defining a first chord across said pipe;
   one or more additional photon sources adapted for attachment at positions on the periphery of said pipe successively closer to the detector, said detector and one or more additional sources defining one or more additional chords across said pipe; and
   a processor adapted to calculate the densities across said first and one or more additional chords of the pipe from the count rate detected by the detector from the first and one or additional sources respectively.

Another aspect of the invention provides the use of an apparatus described above in methods of the invention.

Another aspect of the invention provides a pipe comprising an apparatus as described above.

DETAILED DESCRIPTION OF INVENTION

Figure 1:
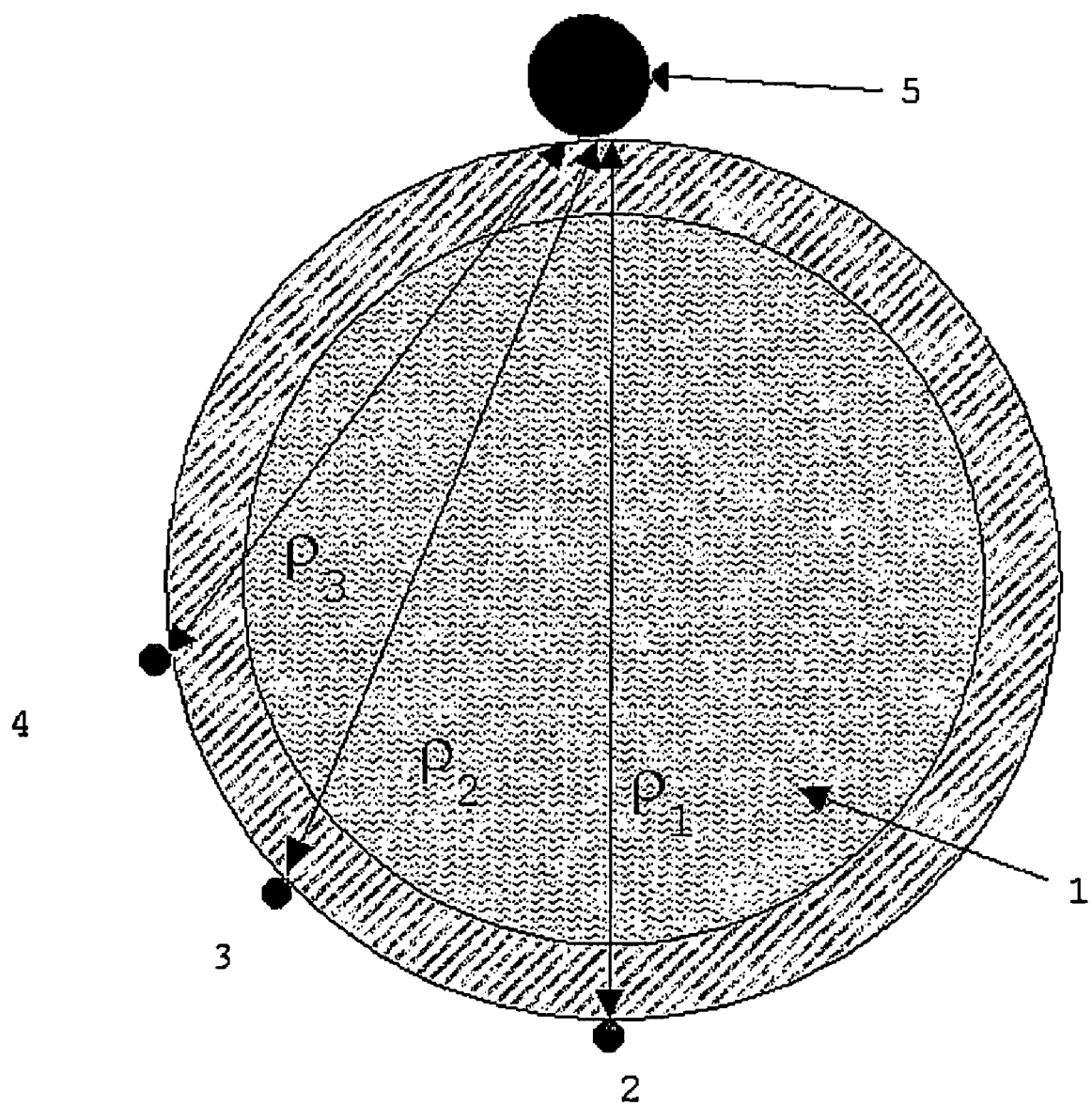
FIG. 1 shows an apparatus according to one embodiment of the invention comprising a detector and 3 gamma ray sources of different energies showing three density measurements along chords ($\rho 1$, $\rho 2$ and $\rho 3$).

In general terms, the present invention relates to the monitoring of mixed or multiphase pipeline flow, in particular the flow and deposition of solids, using, in particular, gamma rays or, alternatively, X-Rays. A preferred approach involves the use of a single gamma ray detector and two or more different gamma ray sources disposed on the periphery of the pipeline.

Photons pass through the flow in the pipeline to the detector and the number of photons received by the detector from a particular source is dependent on the density of the material flowing in the pipe between the source and the detector. The normally stringent requirements for calibration are relaxed thanks to additional positional information contained in the spectroscopic window of each source.

Density based measurements are particularly useful in the case of a mixed flow with low gas fraction, such as a bitumen-water-solids flow, since liquids such as water and bitumen have densities close to 1 g/cc (and need not be treated separately), while solids such as sand have a much higher grain density, typically around 2.65 g/cc. Even loosely aggregated solid with around 40% water-filled pore space will have a bulk density of around 2 g/cc. Thus, density variation provides a highly sensitive signature of in-homogeneity, and therefore solid deposition, in mixed flow pipelines.

As described above, a gamma ray detector may be provided at a first point on the periphery of said pipe and a first gamma ray source is provided at a second point on the periphery of said pipe for example a point opposite the detector, such that the detector and first source define a first chord across the cross-section of the pipe. Practically, the pipeline is cylindrical with a circular cross-section and the detector and the first gamma ray source are positioned on the circumference of said pipeline. However, the pipeline may be of any shape. Preferably, the first source is positioned diametrically opposite the detector.

One or more additional gamma ray sources may be provided at points on the circumference of the pipe successively closer to the detector than the first source. Practically, the detector, the first source and the one or more additional sources are positioned approximately in a same plane, which is generally orthogonal to the axis of said pipe. However, the sources may be located at some short distances from said plane and said plane may be not orthogonal to the pipe axis.

The detector and the additional sources define one or more additional chords of successively decreasing length across said pipe relative to said first chord. The density across said first chord is determined from the count rate detected from the first source by the detector, and; the densities across the one or more additional chords are determined from the count rate detected from the one or more additional sources by the detector.

Deposition or average phase fraction of solid in the pipe may be determined from the relative densities across said first chord and said one or more additional chords.

Measurement of the distribution of solid between the first chord and the one or more additional chords may also be used to measure the tendency of solid in the pipeline to gravitate to a lower part of the flow. This may useful in determining the risk of deposition and/or blockage of the pipeline.

Suitable gamma ray detectors include the Permanent Gamma Ray Gauge (PGRG) used in the FloWatcher densitometer. Scintillators or other detectors can be used.

Suitable gamma ray sources include chemical isotope sources. Preferably, combinations of sources employed in accordance with the invention emit photons of distinct but overlapping energy spectra. Emissions from the different sources are separable using conventional techniques such that the detector can simultaneously measure the emissions from each of the sources independently. Preferably, the first source, which is furthest from the detector, is the highest energy Source and the energy of the sources decreases the nearer they are to the source i.e. the sources may be of successively lower photon energy relative to the first source. For example, the first source may be Co-60 (1175-1333 keV) and the first and second additional sources may be Cs-137 (662 keV) and Ba-133 (80-400 keV).

Low-activity sources (e.g. licence exempt) may be used in accordance with the invention. These may be advantageous for practical reasons including keeping personnel exposure and cost low and simplifying transport documentation. Even with low activity sources, adequate nuclear counting statistics may usually be obtained with counting times of about one minute.

In some preferred embodiments, the detector is positioned at the uppermost point on the circumference of the pipe and the first source is positioned at the lower-most point on the circumference of the pipe (i.e. defining a vertical first chord). Preferably, first source is the highest photon energy source (which is least strongly attenuated). This provides optimal count rate contrast as a function of density across the longest chord. Similarly, lower energy sources may be placed closer to the detector. Source and detector are preferably positioned on the external surface of the pipeline.

The detector preferably measures photon emissions across the energy spectrum. The highest energy events, which arise only from the first source of highest energy, are then identified from this spectral measurement. These events are full energy or so-called "photopeak" events in which the gamma-rays reach the detector unscattered.

Modelling or calibration measurements provide information about the shape of the entire spectrum arising from this first source, including events where Compton scattering gives rise to lower apparent energies. Thus, the total measurement spectrum may be corrected for these scattering events to arrive at a measurement of count rate arising from the first (highest energy) source.

Events from the second highest-energy source (for example the first additional source) may then be identified, and an analogous Compton correction made. By repeating this procedure, count rates from each different source are derived.

Spectroscopic methods suitable for identifying events from various sources and applying an appropriate correction are well known to those skilled in the art.

From the count rates, density across the chord may be determined.

The density measurement across the first chord through the cross section of the pipeline ($\rho_1$ in FIG. 1) provides a hold-up determination for the entire flow in the pipeline. Flow in the pipeline may be stratified, in which case the vertical linear hold-up across the first chord is not always the same as an area-based hold-up measurement. The second and subsequent measurements (e.g. $\rho_2$ and $\rho_3$ in FIG. 1) across the one or more additional chords provide hold-up measurements for progressively higher parts of the flow cross-section. If sand deposition occurs, or if settlement leads to an increased sand fraction in lower parts of the flow, then $\rho_1$ will be clearly higher than $\rho_2$, $\rho_3$ etc. Estimates of the count rates for liquid and solids may be made using an empty pipe, or homogeneously filled pipe. Since the density contrast between liquid (water or bitumen) and sand is large, high-precision knowledge of the count rates is not required. The presence of a significant sand fraction in any of the beam density measurements will easily be observed. Densities are calculated from the counts on the basis of a calibration curve determined from control experiments or modelling.

In some embodiments of the invention, the one or more additional sources may comprise a first and a second additional source. A method of the invention may thus comprise:
providing a first and a second additional gamma ray source, said detector and first and second additional source defining a second and a third chord respectively across said pipe,
determining the density across said first, second and third chords from the count rate detected by the detector from the first, second and third sources, respectively,
determining the deposition of solid in the pipe from the relative densities across said first, second and third chords.

As described above, the first, second and third chords are preferably of successively decreasing length i.e. the first source and the first and second additional sources are positioned successively closer to the detector on the circumference of the pipeline. Preferably, the first source and the first and second additional sources have successively decreasing energies.

In some embodiments, the gamma ray detector may comprise more than one detector module, each said detection module being positioned at the same or a different point on the circumference of the pipe. For example, each module may be configured to detect emission from a particular source species so as to determine the density across a individual chord or pair of chords across the pipeline. However, for minimal cost and complexity, the use of a single detector module for the simultaneous determination of multiple densities across different chords of the pipeline is preferred.

Furthermore, methods and apparatus of the invention may be used to average out, or identify and measure, asymmetric stratification in a pipeline.

Figure 2:
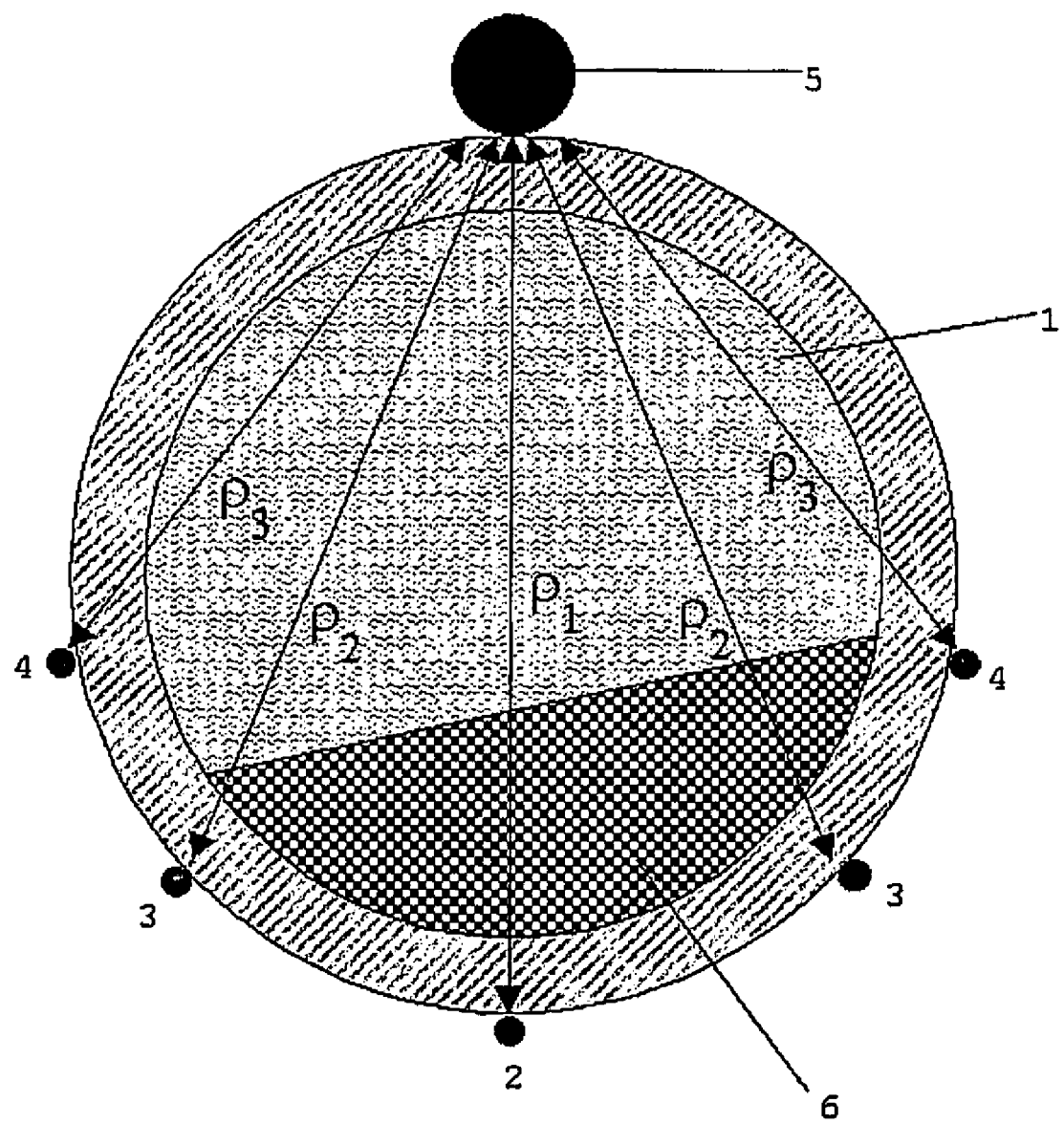
FIG. 2 shows apparatus of another embodiment of the invention comprising a detector and five gamma ray sources of three different energies, the pairs of medium and low energy sources (sources 2 and 3) allowing symmetrical averaging in the case of asymmetric stratification.

In some embodiments, identical gamma ray sources may be placed symmetrically relative to the detector on either side of the pipe, for example at the same vertical position as shown in FIG. 2. In this case, the count rate which is detected from each source species will automatically represent the average hold-up along chords on each side of the pipe.

Thus, in the case of asymmetrically stratified configurations (e.g. sand deposition close to a bend in the pipeline, which may pile up on one side of the pipe), a substantially accurate average hold-up may still be derived. For example, the average value of $\rho_2$ in FIG. 2 will give an approximately correct hold-up for the deposited sand layer.

Figure 3:
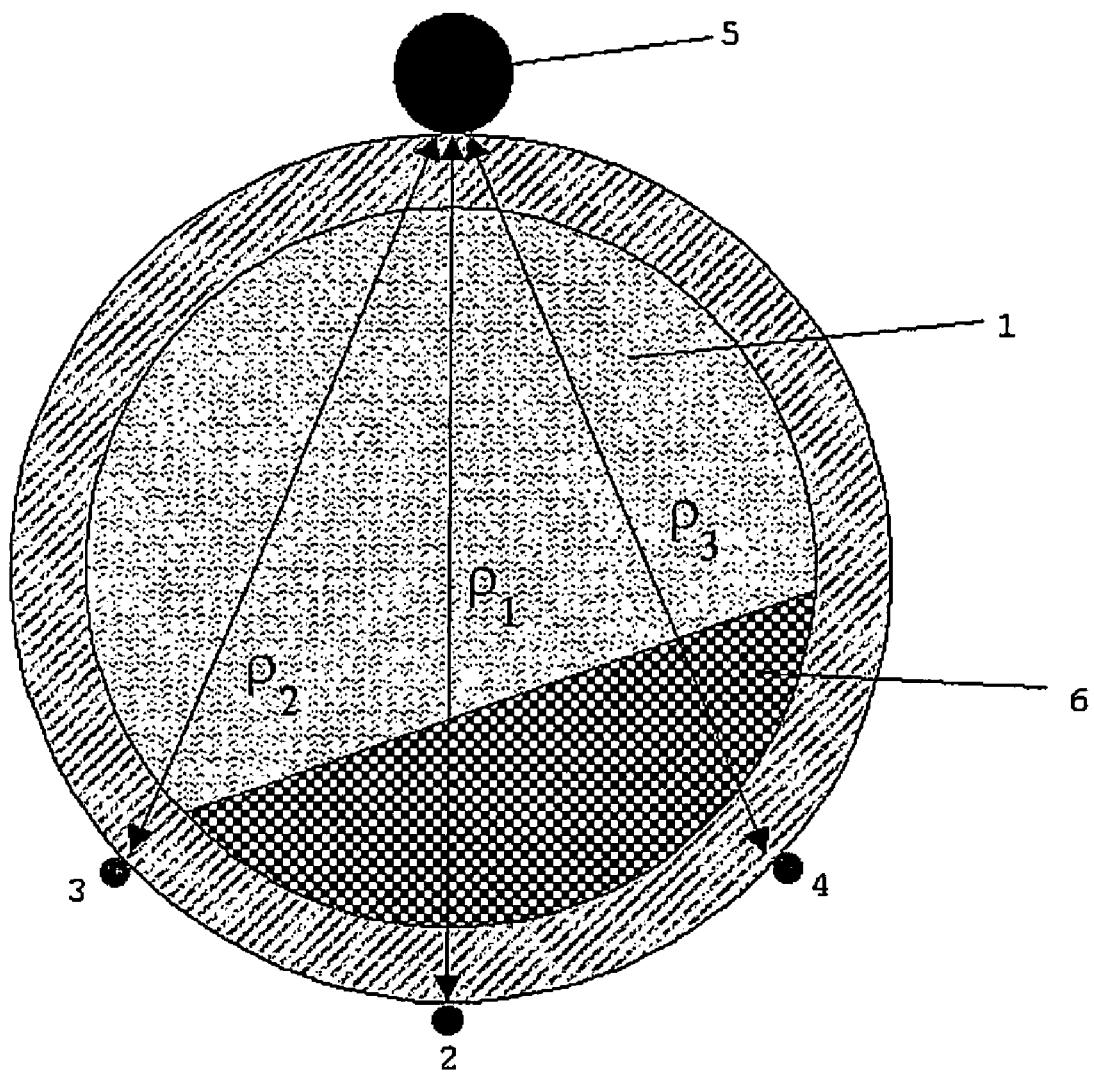
FIG. 3 shows apparatus of another embodiment of the invention comprising a detector and 3 gamma ray sources of different energies showing three density measurements along chords ($\rho 1$, $\rho 2$ and $\rho 3$) arranged for asymmetric sensitivity.

In other embodiments, in which measurement of asymmetric deposition is required, different source species may be arranged symmetrically on either side of the pipe (for example at the same vertical position, as shown in FIG. 3). In the example shown, the hold-up measured across $\rho_3$ will show a significant sand fraction, while the symmetrically placed $\rho_2$ measurement will not indicate the presence of sand.

The invention also provides apparatus for use in performing a method as described above. The apparatus may comprise a detector, a first source and one or more additional sources as described above, all of which are adapted for attachment to the circumference of a pipeline. For example, the apparatus may comprise one or more fixings for attaching the detector and sources to the pipe.

The apparatus may comprise a processor which is connected or connectable to the detector. The processor may identify energy events arising from the first source and the one or more additional sources and apply an appropriate correction for scattering events, as determined by modelling or calibration measurements in order to determine the count rate arising from each individual source. Densities across the individual chords of the pipeline cross-section may then be determined from the counts detected from each source.

FIG. 1 shows an apparatus for monitoring solids in a mixed flow pipeline according to one embodiment of the invention. A gamma ray detector 5 is positioned at a first point on the circumference of the pipe and a first gamma ray source 2 comprising Co-60 (1175-1333 keV) is provided at a point on the circumference of said pipe diametrically opposite the detector 5, such that the detector 5 and first source 2 define a first chord $\rho_1$ across the cross section of said pipe. A second gamma ray source 3 comprising Cs-137 (662 keV) and a third gamma ray source 4 comprising B-133 are positioned at points on the circumference of said pipe successively closer to the detector 5 than the first source 2. The detector 5 and the second source 3 define a chord $\rho_2$ across the pipe and the detector 5 and the third source 4 define a chord $\rho_3$ across the pipe. Chords $\rho_1$, $\rho_2$ and $\rho_3$ being of successively decreasing length.

The density across $\rho_1$ is determined from the count rate detected from the first source by the detector and provides a hold-up determination for the entire flow. The densities across $\rho_2$ and $\rho_3$ are determined from the count rate detected from the second and third sources by the detector and provide hold-up determinations for progressively higher parts of the flow cross section.

FIG. 2 shows an apparatus according to another embodiment of the invention, which is arranged to determine average hold-up across a pipeline having asymmetric stratification. The gamma ray detector 5 and first gamma ray source 2 are positioned as before. A pair of second gamma ray sources 3 comprising Cs-137 (662 keV) are positioned symmetrically on either side of the pipe at the same vertical position and a pair of third gamma ray sources 4 comprising Ba-133 are positioned symmetrically on either side of the pipe at the same vertical position, above the vertical position of the second gamma ray sources 4 in the figure. The chords defined by the pair of second sources 3 with the detector 5 are of identical length and are designated $\rho_2$ and the chords defined by the pair of third sources 4 with the detector 5 are of identical length and are designated $\rho_3$. $\rho_2$ is less than $\rho_1$ and greater than $\rho_3$. In the event of asymmetric stratification as shown in FIG. 2, the average value of $\rho_2$ provides an approximately correct hold-up value for the deposited layer 6.

FIG. 3 shows an apparatus according to another embodiment of the invention, which is arranged to measure asymmetric stratification. The gamma ray detector 5 and first gamma ray source 2 are positioned as before. A second gamma ray source 3 comprising Cs-137 (662 keV) and a third gamma ray source 4 comprising Ba-133 are positioned symmetrically on either side of the pipe at the same vertical position. The chord defined by the second source 3 with the detector 5 is designated $\rho_2$ and the chord defined by the third source 4 with the detector 5 is designated $\rho_3$.

Asymmetric sand deposition 6 in the pipeline will be indicated by a significant sand fraction in the hold-up measured by ρ3 but no sand fraction in the hold-up measured by ρ2 or vice versa.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A method of monitoring flow in a flow pipe, the method comprising:
   providing a flow pipeline having
   a photon detector at a first position on the periphery of said pipe,
   a first photon source at a second position on the periphery of said pipe, said detector and first source defining a first chord across said pipe, and
   one or more additional photon sources at positions on the periphery of said pipe defining one or more additional chords across said pipe, wherein the first photon source and the one or more additional photon sources are of different photon energies;
   determining the density across said first chord from the count rate detected from the first source by the detector; and
   determining the densities across said one or more additional chords from the count rate detected from the one or more additional sources by the detector, wherein the additional chords are chosen to have successively decreasing length across said pipe relative to said first chord.

2. The method according to claim 1 wherein the first source is diametrically opposite the detector.

3. The method according to claim 1 wherein the flow is a mixed flow comprising at least two phases including a solid phase, said method further comprising:
   determining the deposition of solid in the pipe from the relative densities across said first chord and said one or more additional chords.

4. The method according to claim 1 wherein the flow is a mixed flow comprising at least two phases including a solid phase, said method further comprising:
   determining the average phase fraction of solid in the pipe from the densities across said first chord and said one or more additional chords.

5. The method according to claim 1 wherein the first photon source and one or more additional photon sources are of successively decreasing photon energies.

6. The method according to claim 1 wherein the photon sources are chemical isotope sources.

7. The method according to claim 1 wherein the detector is positioned at the uppermost point on the periphery of the pipe and the first source is positioned at the bottommost point on the periphery of the pipe.

8. The method according to claim 1 comprising positioning the detector, the first source and the one or more additional sources on the exterior surface of the pipeline.

9. The method according to claim 1 wherein the one or more additional sources comprise one or more pairs of identical gamma ray sources, each said pair of sources being positioned on the periphery of the pipe such that the chords across the pipe defined by each member of the pair with the detector are approximately of equal length, the average hold-up being determined from the average value of the densities across said chords.

10. The method according to claim 1 wherein the one or more additional sources comprise at least one pair of non-identical sources positioned on the circumference of said pipe, such that the chords across the pipe defined by each member of the pair with the detector are approximately of equal length, the asymmetric deposition of solid in the pipe being determined from the relative density values determined across the chords defined by each member of the pair with the detector.

11. The method of claim 1 wherein the photon detector is a gamma ray detector.

12. The method of claim 1 wherein the first and the one or more additional sources are positioned one the periphery of the pipe successively closer to detector.

13. An apparatus for monitoring flow in a flow pipe comprising;
   a photon detector adapted for attachment at a first point on the periphery of said pipe;
   a first photon source adapted for attachment at the periphery of said pipe opposite the detector, said detector and first source defining a first chord across said pipe;
   one or more additional photon sources adapted for attachment at positions on the periphery of said pipe successively closer to the detector, said detector and one or more additional sources defining one or more additional chords across said pipe, wherein the first photon source and the one or more additional photon sources are of different photon energies; and
   a processor adapted to determine the densities across said first and one or more additional chords of the pipe as a function of the count rate detected by the detector from the first and one or more additional sources, respectively.

14. The apparatus according to claim 13 wherein the detector, the first source and the additional sources are adapted for attachment to the exterior surface of a pipeline.

15. An apparatus for monitoring flow in a pipe comprising:
   a flow pipe having:
   a photon detector adapted for attachment at a first point on the periphery of said pipe;
   a first photon source adapted for attachment at the periphery of said pipe opposite the detector, said detector and first source defining a first chord across said pipe;
   one or more additional photon sources adapted for attachment at positions on the periphery of said pipe successively closer to the detector, said detector and one or more additional sources defining one or more additional chords across said pipe, wherein the first photon source and the one or more additional photon sources are of different photon energies; and
   a processor adapted to determine the densities across said first and one or more additional chords of the pipe as a function of the count rate detected by the detector from the first and one or more additional sources, respectively.

16. A method of monitoring flow in a pipeline comprising:
   Providing a mixed flow pipeline having:
   a photon detector at a first position on the periphery of said pipe,
   a first photon source at a second position on the periphery of said pipe, said detector and first source defining a first chord across said pipe, and
   one or more additional photon sources at positions on the periphery of said pipe defining one or more additional chords across said pipe, wherein the first photon source and the one or more additional photon sources are of different photon energies;
   determining the density across said first chord from the count rate detected from the first source by the detector; and
   determining the densities across said one or more additional chords from the count rate detected from the one or more additional sources by the detector, wherein the additional chords are chosen to have successively decreasing length across said pipe relative to said first chord.

* * * * *